(12) United States Patent
Wu et al.

(10) Patent No.: US 7,780,626 B2
(45) Date of Patent: Aug. 24, 2010

(54) CATHETER SHAFT FOR REGULATION OF INFLATION AND DEFLATION

(75) Inventors: Show-Mean Wu, San Diego, CA (US); Ricardo David Roman, San Diego, CA (US); Fuh-Sheng Chen, San Diego, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1414 days.

(21) Appl. No.: 10/637,142

(22) Filed: Aug. 8, 2003

(65) Prior Publication Data

US 2005/0033225 A1 Feb. 10, 2005

(51) Int. Cl.
*A61M 29/00* (2006.01)
*A61M 25/00* (2006.01)
*A61B 17/22* (2006.01)
*A61D 1/02* (2006.01)

(52) U.S. Cl. .................... 604/96.01; 606/159; 606/192; 606/194; 604/523

(58) Field of Classification Search ................ 606/159, 606/192, 194; 604/96.01, 22, 101.03, 102.01, 604/102.02, 102.03, 915, 917, 921
See application file for complete search history.

(56) References Cited

U.S. PATENT DOCUMENTS

| | | | |
|---|---|---|---|
| 2,816,552 | A | 12/1957 | Hoffman |
| 3,174,851 | A | 3/1965 | Buehler et al. |
| 3,351,463 | A | 11/1967 | Rozner et al. |
| 3,635,223 | A | 1/1972 | Klieman |
| 3,749,085 | A | 7/1973 | Willson et al. |
| 3,753,700 | A | 8/1973 | Harrison et al. |
| 3,990,453 | A | 11/1976 | Douvas et al. |
| 4,140,126 | A | 2/1979 | Choudhury |
| 4,141,364 | A | 2/1979 | Schultze |
| 4,263,236 | A | 4/1981 | Briggs et al. |
| 4,273,128 | A | 6/1981 | Lary |
| 4,292,974 | A | 10/1981 | Fogarty et al. |
| 4,406,656 | A | 9/1983 | Hattler et al. |
| 4,465,072 | A | 8/1984 | Taheri |
| 4,490,421 | A | 12/1984 | Levy |

(Continued)

FOREIGN PATENT DOCUMENTS

DE 34 00 416 A1 7/1985

(Continued)

OTHER PUBLICATIONS

Lary, Banning G., et al., "A Method for Creating a Coronary-Myocardial Artery," *Surgery*, Jun. 1966, vol. 59, No. 6, pp. 1061-1064.

(Continued)

*Primary Examiner*—Nicholas D Lucchesi
*Assistant Examiner*—Ian K Holloway
(74) *Attorney, Agent, or Firm*—Crompton, Seager & Tufte, LLC (57) ABSTRACT

An angioplasty balloon catheter and method of making and using the same. The balloon catheter may include a catheter shaft and a balloon coupled to the shaft. The balloon may include one or more cutting edges coupled thereto. The shaft may include one or more inflation lumens and a plurality of openings defined therein that are in fluid communication with the inflation lumen or lumens.

25 Claims, 5 Drawing Sheets

U.S. PATENT DOCUMENTS

| | | | |
|---|---|---|---|
| 4,572,186 A | 2/1986 | Gould et al. |
| 4,574,781 A | 3/1986 | Chin |
| 4,608,984 A | 9/1986 | Fogarty |
| 4,627,436 A | 12/1986 | Leckrone |
| 4,685,458 A | 8/1987 | Leckrone |
| 4,686,982 A | 8/1987 | Nash |
| 4,696,667 A | 9/1987 | Masch |
| 4,705,517 A | 11/1987 | DiPisa, Jr. |
| 4,723,549 A | 2/1988 | Wholey et al. |
| 4,728,319 A | 3/1988 | Masch |
| 4,747,405 A | 5/1988 | Leckrone |
| 4,748,982 A | 6/1988 | Horzewski et al. |
| 4,784,636 A | 11/1988 | Rydell |
| 4,787,388 A | 11/1988 | Hofmann |
| 4,790,813 A | 12/1988 | Kensey |
| 4,793,348 A | 12/1988 | Palmaz |
| 4,796,629 A | 1/1989 | Grayzel |
| 4,799,479 A | 1/1989 | Spears |
| RE32,983 E | 7/1989 | Levy |
| 4,886,061 A | 12/1989 | Fischell et al. |
| 4,921,483 A | 5/1990 | Wijay et al. |
| 4,921,484 A | 5/1990 | Hillstead |
| 4,936,845 A | 6/1990 | Stevens |
| 4,966,604 A | 10/1990 | Reiss |
| RE33,561 E | 3/1991 | Levy |
| 5,009,659 A | 4/1991 | Hamlin et al. |
| 5,030,201 A | 7/1991 | Palestrant |
| 5,042,985 A | 8/1991 | Elliott et al. |
| 5,047,040 A | 9/1991 | Simpson et al. |
| 5,049,132 A | 9/1991 | Shaffer et al. |
| 5,078,722 A | 1/1992 | Stevens |
| 5,078,725 A | 1/1992 | Enderle et al. |
| 5,085,662 A | 2/1992 | Willard |
| 5,087,265 A | 2/1992 | Summers |
| 5,100,424 A | 3/1992 | Jang et al. |
| 5,100,425 A | 3/1992 | Fischell et al. |
| 5,102,390 A | 4/1992 | Crittenden et al. |
| 5,116,318 A | 5/1992 | Hillstead |
| 5,135,482 A | 8/1992 | Neracher |
| 5,152,773 A | 10/1992 | Redha |
| 5,156,594 A | 10/1992 | Keith |
| 5,156,610 A | 10/1992 | Reger |
| 5,158,564 A | 10/1992 | Schnepp-Pesch et al. |
| 5,176,693 A | 1/1993 | Pannek, Jr. |
| 5,180,368 A | 1/1993 | Garrison |
| 5,196,024 A * | 3/1993 | Barath | 606/159 |
| 5,209,749 A | 5/1993 | Buelna |
| 5,209,799 A | 5/1993 | Vigil |
| 5,226,430 A | 7/1993 | Spears et al. |
| 5,226,887 A | 7/1993 | Farr et al. |
| 5,248,311 A | 9/1993 | Black et al. |
| 5,250,059 A | 10/1993 | Andreas et al. |
| 5,300,025 A | 4/1994 | Wantink |
| 5,318,576 A | 6/1994 | Plassche, Jr. et al. |
| 5,320,634 A | 6/1994 | Vigil et al. |
| 5,328,472 A | 7/1994 | Steinke et al. |
| 5,336,234 A | 8/1994 | Vigil et al. |
| 5,372,601 A | 12/1994 | Lary |
| 5,395,361 A | 3/1995 | Fox et al. |
| 5,411,466 A | 5/1995 | Hess |
| 5,415,654 A | 5/1995 | Daikuzono |
| 5,417,653 A | 5/1995 | Sahota et al. |
| 5,417,703 A | 5/1995 | Brown et al. |
| 5,425,711 A | 6/1995 | Ressemann et al. |
| 5,437,659 A | 8/1995 | Leckrone |
| 5,441,510 A | 8/1995 | Simpson et al. |
| 5,456,681 A | 10/1995 | Hajjar |
| 5,496,308 A | 3/1996 | Brown et al. |
| 5,507,760 A | 4/1996 | Wynne et al. |
| 5,507,761 A | 4/1996 | Duer |
| 5,522,818 A | 6/1996 | Keith et al. |
| 5,522,825 A | 6/1996 | Kropf et al. |
| 5,549,556 A | 8/1996 | Ndondo-Lay et al. |
| 5,569,195 A | 10/1996 | Saab |
| 5,569,277 A | 10/1996 | Evans et al. |
| 5,571,087 A | 11/1996 | Ressemann et al. |
| 5,616,149 A * | 4/1997 | Barath | 606/159 |
| 5,628,761 A | 5/1997 | Rizik |
| 5,643,296 A | 7/1997 | Hundertmark et al. |
| 5,645,529 A | 7/1997 | Fagan et al. |
| 5,681,336 A | 10/1997 | Clement et al. |
| 5,697,944 A | 12/1997 | Lary |
| 5,713,913 A | 2/1998 | Lary et al. |
| 5,718,684 A | 2/1998 | Gupta |
| 5,720,724 A | 2/1998 | Ressemann et al. |
| 5,792,105 A | 8/1998 | Lin et al. |
| 5,827,201 A | 10/1998 | Samson et al. |
| 5,860,954 A | 1/1999 | Ropiak |
| 5,895,402 A | 4/1999 | Hundertmark et al. |
| 5,931,819 A | 8/1999 | Fariabi |
| 5,941,871 A * | 8/1999 | Adams et al. | 604/523 |
| 6,024,722 A | 2/2000 | Rau et al. |
| 6,039,699 A | 3/2000 | Viera |
| 6,066,149 A | 5/2000 | Samson et al. |
| 6,066,157 A * | 5/2000 | Barbere | 606/194 |
| 6,068,623 A | 5/2000 | Zadno-Azizi et al. |
| 6,139,510 A | 10/2000 | Palermo |
| 6,142,975 A | 11/2000 | Jalisi et al. |
| 6,165,140 A | 12/2000 | Ferrera |
| 6,165,167 A | 12/2000 | Delaloye |
| 6,165,292 A | 12/2000 | Abrams et al. |
| 6,168,571 B1 | 1/2001 | Solar et al. |
| 6,190,332 B1 | 2/2001 | Muni et al. |
| 6,193,686 B1 | 2/2001 | Estrada et al. |
| 6,217,549 B1 | 4/2001 | Selmon et al. |
| 6,217,567 B1 | 4/2001 | Zadno-Azizi et al. |
| 6,241,690 B1 | 6/2001 | Burkett et al. |
| 6,254,550 B1 | 7/2001 | McNamara et al. |
| 6,306,105 B1 | 10/2001 | Rooney et al. |
| 6,306,151 B1 | 10/2001 | Lary |
| 6,344,029 B1 | 2/2002 | Estrada et al. |
| 6,355,016 B1 | 3/2002 | Bagaoisan et al. |
| 6,383,146 B1 | 5/2002 | Klint |
| 6,387,075 B1 | 5/2002 | Stivland et al. |
| 6,398,798 B2 | 6/2002 | Selmon et al. |
| 6,409,863 B1 | 6/2002 | Williams et al. |
| 6,425,882 B1 | 7/2002 | Vigil |
| 6,458,076 B1 | 10/2002 | Pruitt |
| 6,471,673 B1 | 10/2002 | Kastenhofer |
| 6,533,754 B1 | 3/2003 | Hisamatsu et al. |
| 6,544,276 B1 | 4/2003 | Azizi |
| 6,648,854 B1 * | 11/2003 | Patterson et al. | 604/96.01 |
| 6,951,566 B2 * | 10/2005 | Lary | 606/159 |
| 6,953,470 B2 * | 10/2005 | Holman et al. | 606/194 |
| 7,279,002 B2 * | 10/2007 | Shaw et al. | 623/1.11 |
| 2006/0106336 A1 * | 5/2006 | Saab | 604/96.01 |
| 2006/0129175 A1 * | 6/2006 | Griffin et al. | 606/192 |

FOREIGN PATENT DOCUMENTS

| | | |
|---|---|---|
| DE | 3402573 | 8/1985 |
| DE | 35 19 626 A1 | 12/1986 |
| EP | 0 291 170 A1 | 11/1988 |
| EP | 0 414 350 A1 | 2/1991 |
| GB | 1 547 328 | 6/1979 |
| WO | WO 90/07909 A1 | 7/1990 |
| WO | WO 91/17714 A1 | 11/1991 |

OTHER PUBLICATIONS

Lary, Banning G., "A Method to Create and Correct Stenosis of a Coronary Artery," *Archives of Surgery*, Nov. 1966, vol. 93, pp. 828-830.

Lary, Banning G., "An Epicaridal Purse String Suture for Closing Coronary Arteriotomy," *The American Surgeon*, Mar. 1967, vol. 33, No. 3, pp. 213-214.

Lary, Banning G., "Coronary Artery Incision and Dilation," *Archives of Surgery*, Dec. 1980, vol. 115, pp. 1478-1480.

Lary, Banning G., "Coronary Artery Resection and Replacement by a Blood Conduit," *Surgery*, Apr. 1969, vol. 65, No. 4, pp. 584-589.

Lary, Banning G., "Effect of Endocardial Incisions on Myocardial Blood Flow,"*Archives of Surgery*, Sep. 1963, vol. 87, pp. 424-427.

Lary, B.G., "Experimental Maintenance of Life by Intravenous Oxygen, Preliminary Report," *Clinical Congress of the American College of Surgeons*, San Francisco, Nov. 5-9, 1951, pp. 30-35.

Lary, Banning G., et al., "Experimental Vein Angioplasty of the Circumflex Coronary Artery," *Journal of Surgical Research*, Sep. 1974, vol. 17, No. 3, pp. 210-214.

Lary, Banning G., "Method for Increasing the Diameter of Long Segments of the Coronary Artery," *The American Surgeon*, Jan. 1966, vol. 32, No. 1, pp. 33-35.

Lary, Banning G., et al., "Myocardial Revascularization Experiments Using the Epicardium," *Archives of Surgery*, Jan. 1969, vol. 98, pp. 69-72.

Lary, Banning G., "Onlay Vein Graft for the Correction of Coronary Artery Obstruction," *Surgery*, Apr. 1966, vol. 59, No. 4, pp. 547-551.

Lary, Banning G., "Surgery for Coronary Artery Disease," *Nursing Clinics of North America*, Sep. 1967, vol. 2, No. 3, pp. 537-542.

Lary, Banning G., et al.. "The 'Coronary Myocardial Artery' for Coronary Artery Disease," *Diseases of the Chest*, Apr. 1996, vol. 49, No. 4, pp. 412-419.

* cited by examiner

CATHETER SHAFT FOR REGULATION OF INFLATION AND DEFLATION

FIELD OF THE INVENTION

The present invention pertains to angioplasty and angioplasty balloon catheters. More particularly, the present invention pertains to angioplasty balloon catheters that include one or more cutting edges.

BACKGROUND OF THE INVENTION

Heart and vascular disease are major problems in the United States and throughout the world. Conditions such as atherosclerosis result in blood vessels becoming blocked or narrowed. This blockage can result in lack of oxygenation of the heart, which has significant consequences since the heart muscle must be well oxygenated in order to maintain its blood pumping action.

Occluded, stenotic, or narrowed blood vessels may be treated with a number of relatively non-invasive medical procedures including percutaneous transluminal angioplasty (PTA), percutaneous transluminal coronary angioplasty (PTCA), and atherectomy. Angioplasty techniques typically involve the use of a balloon catheter. The balloon catheter is advanced over a guidewire so that the balloon is positioned adjacent a stenotic lesion. The balloon is then inflated, and the restriction of the vessel is opened.

One of the major obstacles in treating coronary artery disease and/or treating blocked blood vessels is re-stenosis. Evidence has shown that cutting the stenosis, for example with an angioplasty balloon equipped with a cutting blade, during treatment can, in some situations, reduce the incidence of re-stenosis in some situations. Additionally, cutting the stenosis may reduce trauma at the treatment site and/or may reduce the trauma to adjacent healthy tissue. Cutting blades may also be beneficial additions to angioplasty procedures when the targeted occlusion is hardened or calcified. It is believed typical angioplasty balloons, alone, may not be able to expand these hardened lesions. Thus, angioplasty balloons equipped with cutting edges have been developed to attempt to enhance angioplasty treatments. There is an ongoing need for improved angioplasty devices, including cutting angioplasty balloons, and improved methods of treating intravascular stenoses and occlusions.

SUMMARY OF THE INVENTION

The present invention relates to angioplasty balloon catheters. In at least some embodiments, an example balloon catheter may include a catheter shaft having a balloon coupled thereto. The balloon may include one or more cutting members or blades attached thereto. Additionally, the shaft may include one or more inflation lumens and a plurality of openings in fluid communication with the inflation lumen or lumens that may, for example, improve the regulation of inflation and deflation as well as improve the folding and refolding abilities of the balloon. These and other features are described in more detail below.

DETAILED DESCRIPTION OF THE INVENTION

The following description should be read with reference to the drawings wherein like reference numerals indicate like elements throughout the several views. The detailed description and drawings illustrate example embodiments of the claimed invention.

Figure 1:
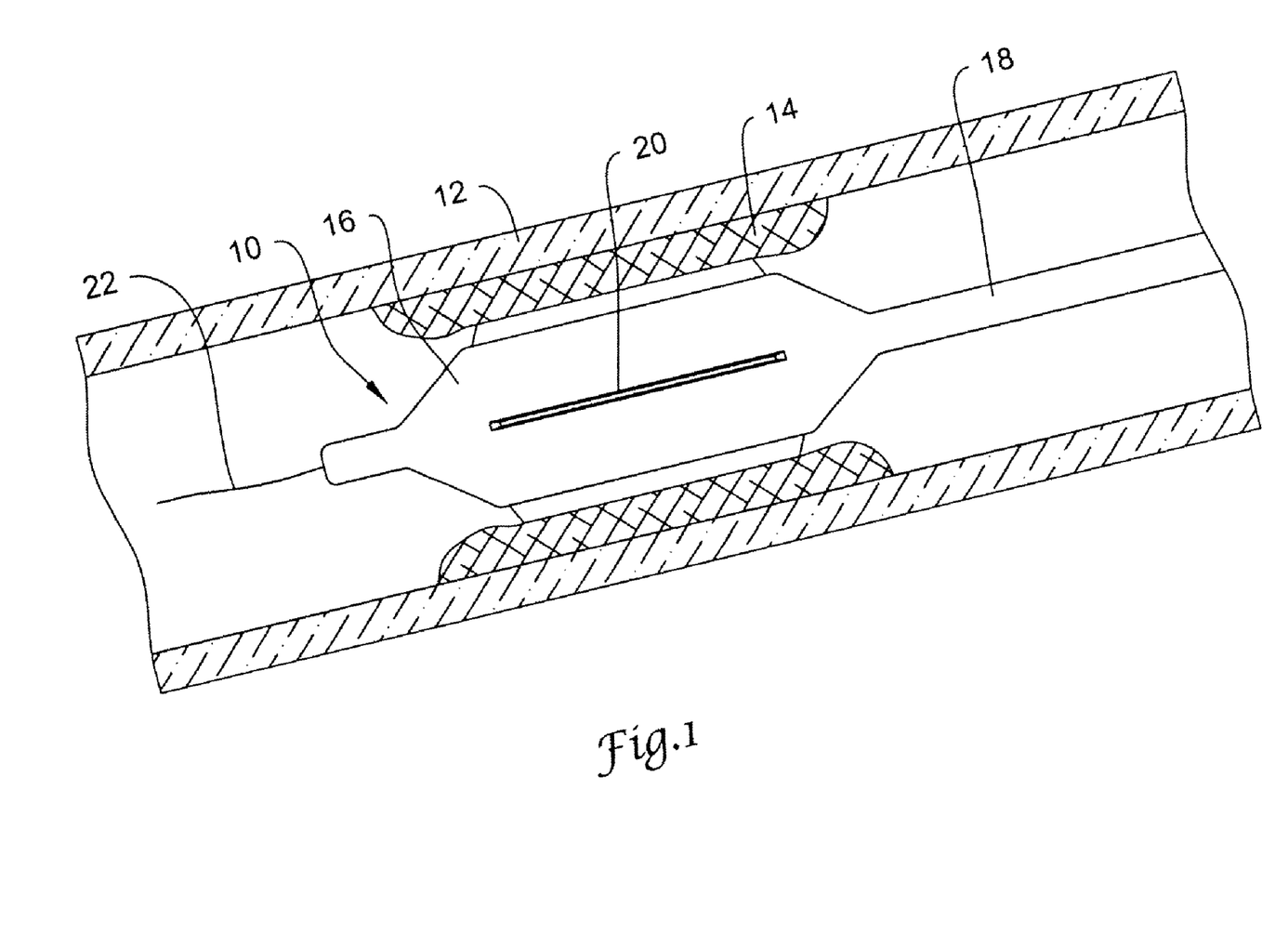
FIG. 1 is a partial cross-sectional side view of a vessel lumen having an example schematic medical device disposed therein.

Angioplasty techniques that include the use of an angioplasty balloon with cutting blades attached thereto have been shown to be a desirable treatment modality for at least some intravascular interventions. FIG. 1 illustrates an example angioplasty catheter 10 positioned in a blood vessel 12 adjacent an intravascular lesion or stenosis 14. Catheter 10 may include a balloon 16 coupled to a catheter shaft 18. Balloon 16 may include one or more cutting members 20 that can be used to cut or sever lesion 14. In general, catheter 10 may be advanced over a guidewire 22 through the vasculature to a target area. Balloon 16 can then be inflated to expand lesion 14 and cutting members 20 can cut lesion 14. The target area may be within any suitable peripheral or cardiac location.

Figure 2:
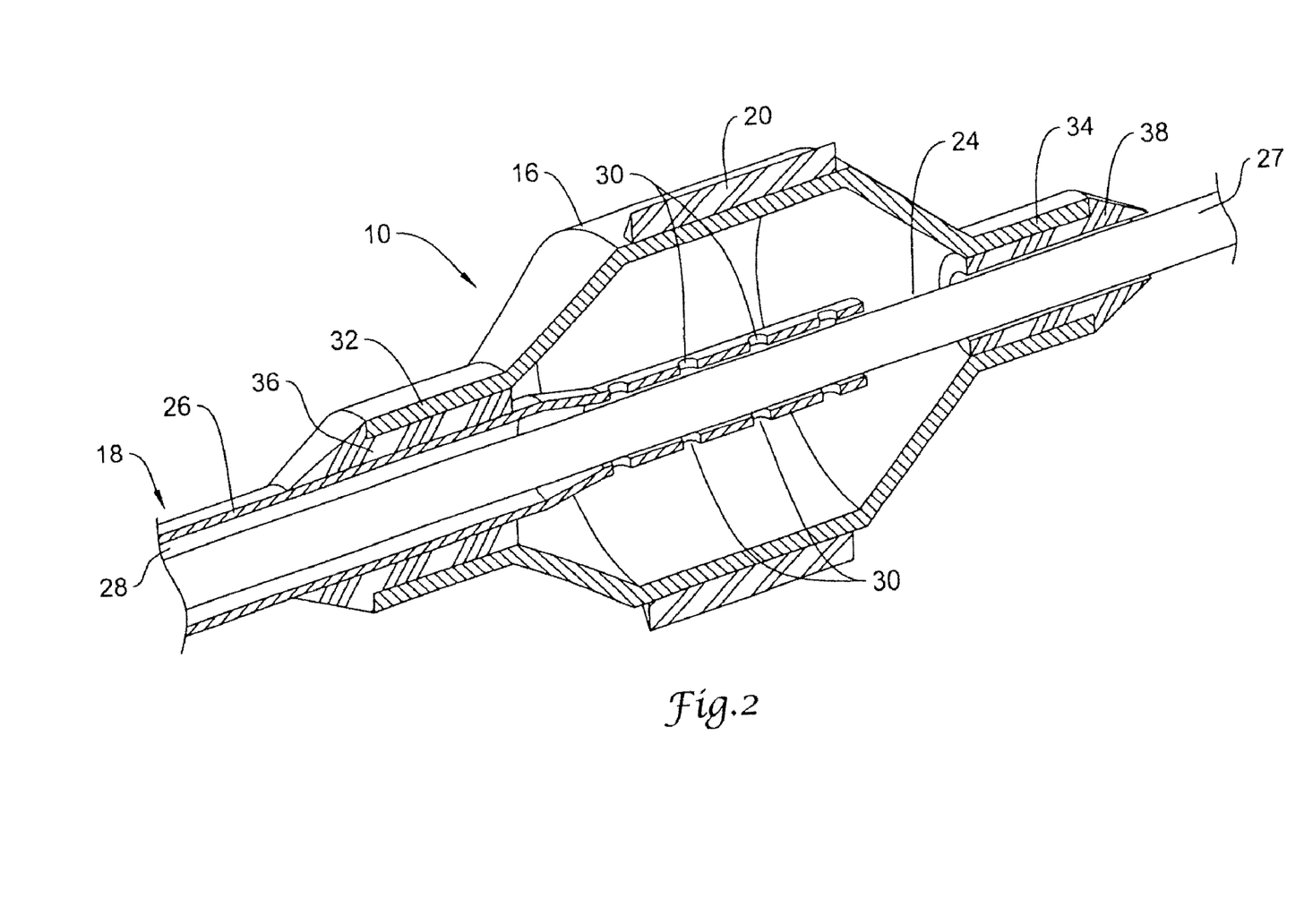
FIG. 2 is a cross-sectional view of an example medical device.

Catheter shaft 18 may include an inner tubular member 24 and an outer tubular member 26, as shown in FIG. 2. Inner tubular member 24 may include an inner lumen 27 that may be, for example, configured for having guidewire 22 disposed therein. Outer tubular member 26 may be generally disposed over inner tubular member 24 so that an inflation lumen 28 may be defined in the space therebetween. In some embodiments, the distal end of outer tubular member 26 may be open so that inflation media can pass through inflation lumen 28 and out of the distal end to inflate balloon 16. In other embodiments, outer tubular member 26 may extend into the expandable portion of balloon 16 and include a plurality of openings 30. Accordingly, inflation media can pass through inflation lumen 28, through openings 30, and into balloon 16.

A plurality of selectively positioned openings 30 within outer tubular member 26 may be desirable for a number of reasons. For example, openings 30 may allow for greater regulation and control during inflation and deflation of balloon 16. This is because openings 30 can allow inflation media to be distributed along essentially the entire length of balloon 16 as well as across a greater portion of the balloon area. Accordingly, inflation and deflation can be regulated and controlled with greater consistency.

The number of openings 30 may vary. For example, outer tubular member 26 may include two or more, three or more, four or more, eight or more, sixteen or more, twenty or more, or any other suitable number of openings 30. Openings 30 may be dispersed in a number of different patterns and arrangements. For example, openings 30 may be grouped into one or more longitudinally aligned sets. However, openings 30 need not be longitudinally aligned or arranged in sets or groups. In FIG. 2, two opposing sets of openings 30, positioned near the top and bottom of outer tubular member 26, are illustrated. It can be appreciated that this example balloon 16 may also include two additional opposing sets generally disposed along the front and rear faces of outer tubular member 26 but that are not visible in this partial cross-sectional view. The number of sets of openings 30 can vary in various embodiments and is not intended to be limited to any particular number. For example, outer tubular member 26 may include two, three, four, five, six, or more sets of openings 30. Of course, the number of openings 30 in each set may also vary and need not be the same among sets for a given outer tubular member 26.

In addition, it may be desirable to position openings 30 or sets of openings 30 directly under cutting members 20 so that openings 30 and cutting members 20 are radially aligned. This may provide more specific inflation forces or pressures adjacent cutting members 20 so that they may more easily move or expand radially outward. This may also help to improve inflation and deflation by regulating in-flow and down-flow of inflation media through balloon 16 and along or adjacent cutting members 20. Additionally, radially aligning openings 30 and cutting members 20 may also reduce twisting of balloon 16 during inflation that might otherwise create sheer forces between cutting members 20 and balloon 16.

In some embodiments, balloon 16 deflation may include venting inflation media. In some other embodiments, deflation may include applying a vacuum to lumen 24. Because of the arrangement of openings 30, venting and/or applying a vacuum to lumen 24 may allow regions of balloon 16 that are adjacent openings 30 to re-fold or deflate first. Accordingly, balloon 16 may have a more consistent and predictable re-folding pattern. In addition, radially and longitudinally aligning openings 30 with cutting members 20 may allow portions of balloon 16 that have cutting members 20 attached to be among the first portions to be deflated or moved radially inward. This allows cutting members 20 to be moved inward prior to removal of catheter 10 and away from where they might otherwise contact and, possibly, damage tissue that was not intended to be cut. Moreover, deflating balloon 16 adjacent cutting members 20 first may allow other "wing portions" of balloon 16 (i.e., those portions between cutting members 20 that may remain somewhat outward when deflation is occurring or has occurred) that may roll over or cover cutting members 20.

Balloon 16 may be made from typical angioplasty balloon materials including polymers such as polyethylene terephthalate (PET), polyetherimid (PEI), polyethylene (PE), etc. Some other examples of suitable polymers may include polytetrafluoroethylene (PTFE), ethylene tetrafluoroethylene (ETFE), fluorinated ethylene propylene (FEP), polyoxymethylene (POM), polybutylene terephthalate (PBT), polyether block ester, polyurethane, polypropylene (PP), polyvinylchloride (PVC), polyether-ester (for example, a polyether-ester elastomer such as ARNITEL® available from DSM Engineering Plastics), polyester (for example, a polyester elastomer such as HYTREL® available from DuPont), polyamide (for example, DURETHAN® available from Bayer or CRISTAMID® available from Elf Atochem), elastomeric polyamides, block polyamide/ethers, polyether block amide (PEBA, for example, available under the trade name PEBAX®), silicones, Marlex high-density polyethylene, Marlex low-density polyethylene, linear low density polyethylene (for example, REXELL®), polyetheretherketone (PEEK), polyimide (PI), polyphenylene sulfide (PPS), polyphenylene oxide (PPO), polysulfone, nylon, perfluoro (propyl vinyl ether) (PFA), other suitable materials, or mixtures, combinations, copolymers thereof, polymer/metal composites, and the like.

In some embodiments, it may be desirable to use high modulus or generally stiffer materials so as to reduce balloon elongation. The above list of materials includes some examples of higher modulus materials. Some other examples of stiffer materials include polymers blended with liquid crystal polymer (LCP) as well as the materials listed above. For example, the mixture can contain up to about 20% LCP. Additionally, due to the relative inelasticity of cutting members 20, balloon elongation could create shear forces between cutting members 20 and balloon 16. Thus, reducing balloon elongation may also help maintain the integrity of the coupling between balloon 16 and cutting members 20.

Tubular members 24/26 may be manufactured from a number of different materials. For example, tubular members 24/26 may be made of metals, metal alloys, polymers, metal-polymer composites, or any other suitable materials. Some examples of suitable metals and metal alloys include stainless steel, such as 304V, 304L, and 316L stainless steel; nickel-titanium alloy such as linear-elastic or super-elastic nitinol, nickel-chromium alloy, nickel-chromium-iron alloy, cobalt alloy, tungsten or tungsten alloys, MP35-N (having a composition of about 35% Ni, 35% Co, 20% Cr, 9.75% Mo, a maximum 1% Fe, a maximum 1% Ti, a maximum 0.25% C, a maximum 0.15% Mn, and a maximum 0.15% Si), hastelloy, monel 400, inconel 825, or the like; or other suitable material. Some examples of suitable polymers include those described above in relation to balloon 16.

Tubular members 24/26 may be arranged in any appropriate way. For example, in some embodiments, inner tubular member 24 can be disposed coaxially within outer tubular member 26. According to these embodiments, inner and outer tubular members 24/26 may or may not be secured to one another along the general longitudinal axis of catheter shaft 18. Alternatively, inner tubular member 24 may follow the inner wall or otherwise be disposed adjacent the inner wall of outer tubular member 26. Again, inner and outer tubular members 24/26 may or may not be secured to one another. For example, inner and outer tubular members 24/26 may be bonded, welded (including tack welding or any other welding technique), or otherwise secured at a bond point. In some embodiments, the bond point may be generally disposed near the distal end of catheter shaft 18. However, one or more bond points may be disposed at any position along shaft 18. In one preferred embodiment, the outer shaft 26 is sealingly bonded to the outer surface of inner shaft 24 distal of the holes 30 so that inflation fluid does not enter the balloon through the end of the outer shaft lumen. The bond may desirably impact, for example, the stability and the ability of tubular members 24/26 to maintain their position relative to one another. In still other embodiments, inner and outer tubular member 24/26 may be substantially parallel to one another so that they are non-overlapping. In these embodiments, shaft 18 may include an outer sheath that is disposed over tubular members 24/26.

In some embodiments, one or more marker members (not shown) may be coupled to catheter 10. The marker members (e.g., marker bands, coils, etc.) may include, be made from, be doped with, or otherwise include a radiopaque material. Radiopaque materials are understood to be materials capable of producing a relatively bright image on a fluoroscopy screen or another imaging technique during a medical procedure. This relatively bright image aids the user of catheter 10 in determining its location. Some examples of radiopaque materials can include, but are not limited to, gold, platinum, palladium, tantalum, tungsten alloy, plastic material loaded with a radiopaque filler, and the like.

Balloon 16 may be coupled to catheter shaft 18 in any of a number of suitable ways. For example, balloon 16 may be adhesively or thermally bonded to shaft 18. In some embodiments, a proximal waist portion 32 of balloon 16 may be bonded to shaft 18, for example at outer tubular member 26, and a distal waist portion 34 may be bonded to shaft 18, for example at inner tubular member 24. A proximal bond 36 and a distal bond 38, which each may represent an adhesive, thermal, mechanical, or other type of connection, may be disposed adjacent proximal and distal waist portions 32/34. The exact bonding positions, however, may vary. A folding spring (not shown) may be coupled to balloon 16, for example adjacent proximal portion 36, which may further help in balloon folding and refolding. A description of a suitable folding spring can be found in U.S. Pat. No. 6,425,882, which is incorporated herein by reference.

Figure 3:
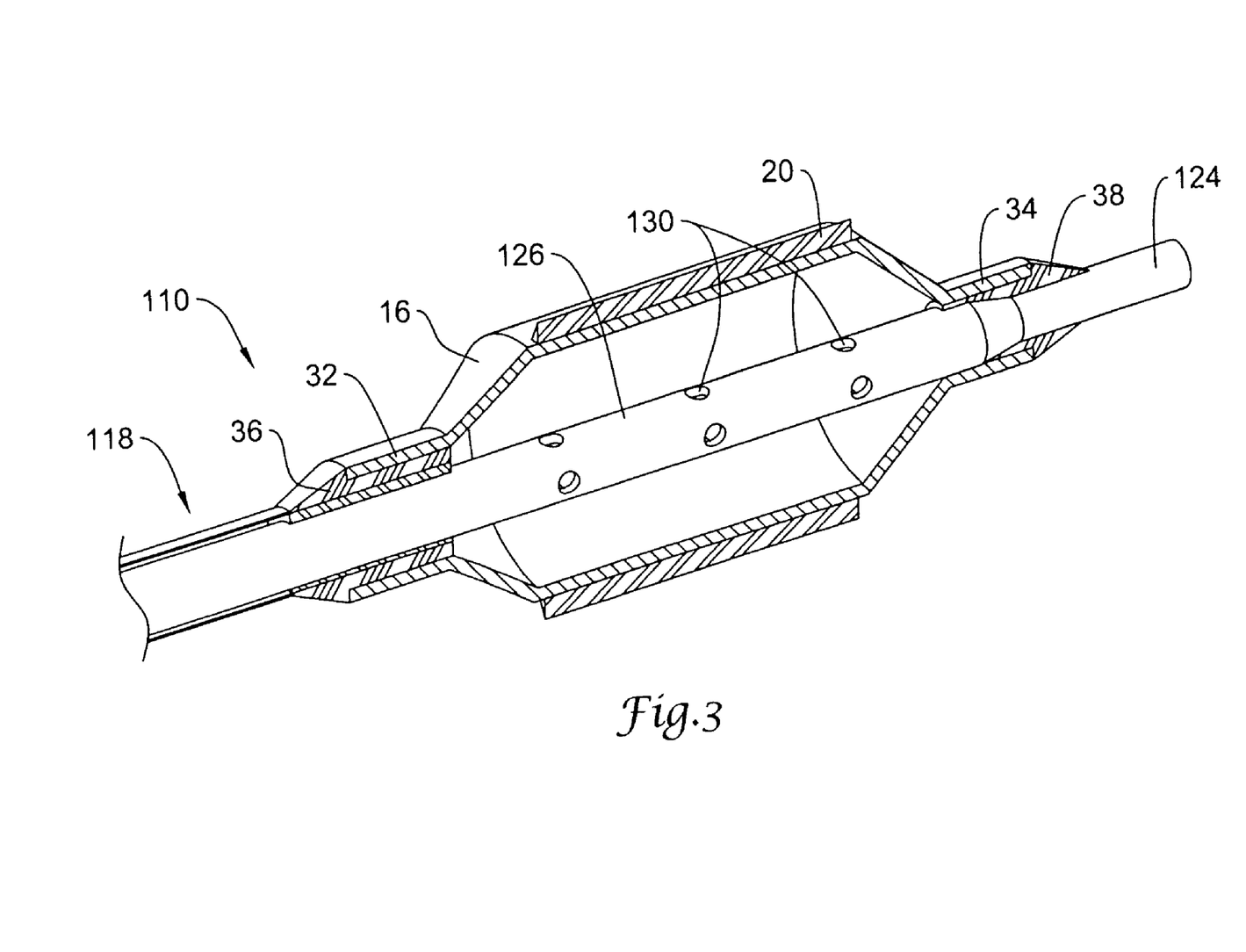
FIG. 3 is a cross-sectional view of another example medical device.

Another example catheter 110 is shown in FIG. 3. Catheter 110 is similar to catheter 10 except that shaft 118 includes outer tubular member 126 that extends distally to a position adjacent distal waist portion 34 of balloon 16. This embodiment of shaft 118 allows balloon 16 to be attached at both its proximal and distal ends (e.g., waist portions 32/34) to outer tubular member 126, which may help to reduce balloon elongation as well as have other desirable effects. Also shown in FIG. 3 is a different number of openings 130 (in this case, a set of three openings 130) defined in outer tubular member 126. This simply demonstrates that a variety of different numbers and patterns of openings 130 may be used in any of the several catheter embodiments.

Figure 4:
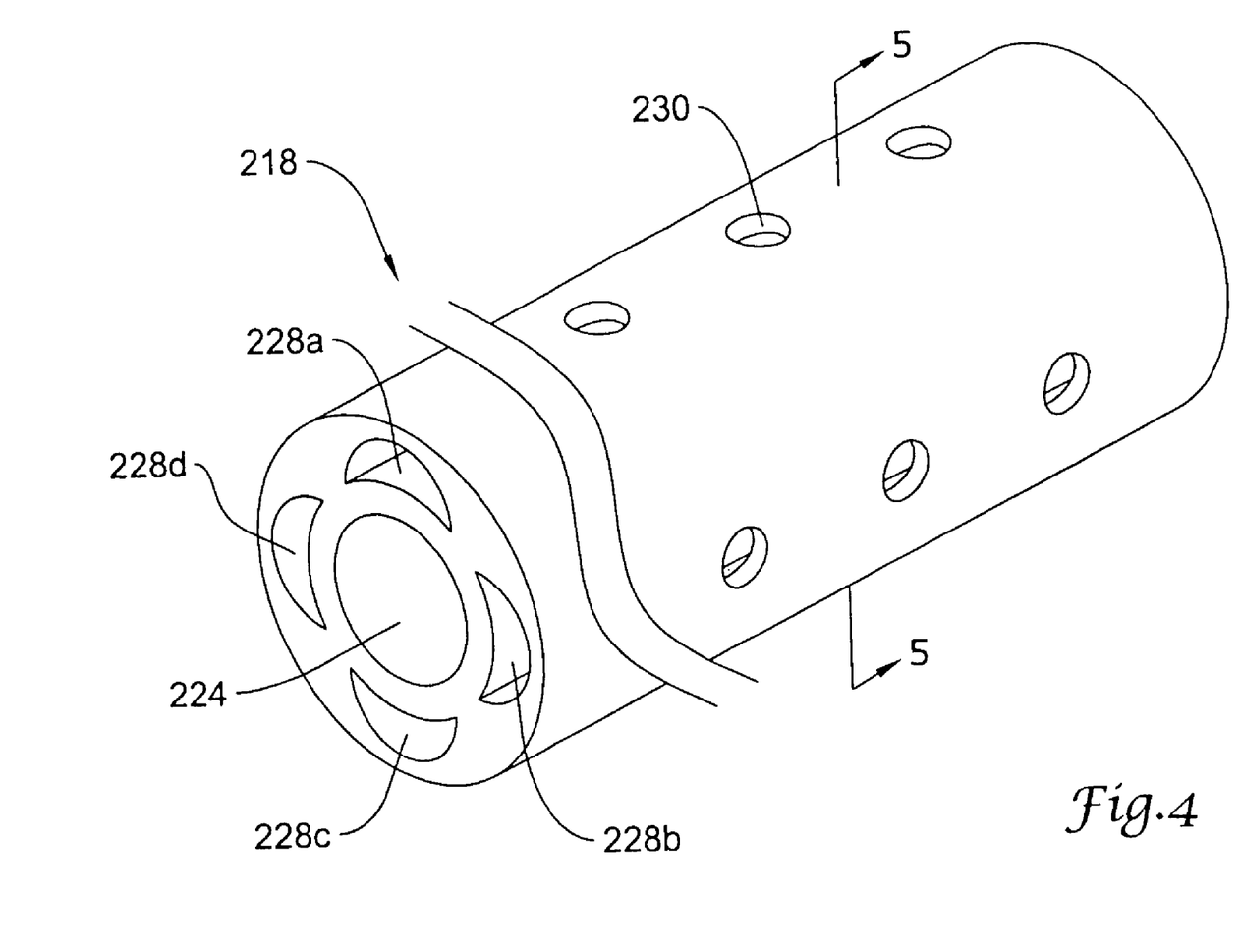
FIG. 4 is a perspective view of a portion of an example catheter shaft.

A perspective view of another example shaft 218, suitable for use with any of the catheters described herein, is shown in FIG. 4. With this embodiment, a single multi-lumen shaft is utilized. Shaft 218 may include a plurality of lumens. For example, a centrally located lumen 224, which may serve as a guidewire lumen, may extend through essentially the middle of shaft 218 and along the length thereof. Additionally, a plurality of side lumens 228*a/b/c/d* may be defined in shaft 218. Balloon 16 can be attached to shaft 218 in a manner that is similar to what is described above.

Side lumens 228*a/b/c/d* may be disposed radially from lumen 224. Of course, the number of lumens 228*a/b/c/d* can vary and is not intended to be limited to four as shown. For example, shaft 218 may include two, three, five, six, or more lumens similar to lumens 228*a/b/c/d*. In at least some embodiments, lumens 228*a/b/c/d* are each coupled to openings 230 or a set of openings 230. Accordingly, the number of lumens 228*a/b/c/d* may be correlated to the number of sets of openings 230. For example, shaft 218 may include four lumens 228*a/b/c/d* when four sets of longitudinally-aligned openings 230 are defined in shaft 218. By including lumens 228*a/b/c/d*, inflation media can be directed to each set of openings 230 through one of lumens 228*a/b/c/d*. This may be desirable, for example, because it may allow each set of openings 230 to be controlled independently of one another.

Shaft 218 may also be desirable because it need not include both inner and outer tubular members. This is because the multi-lumen configuration of shaft 218 is configured for both advancement over a guidewire and for inflating balloon 16. In addition, because fewer structural elements are included, shaft 218 may be constructed to have a lower profile than typical angioplasty catheter shafts and allow shaft 218 to be used in catheters that target smaller or more sensitive vascular locations such as the brain.

Shaft 218 may be manufactured from any suitable material including the metals and polymers listed above as well as other appropriate material. The material chosen can be processed in order to define a shape and configuration similar to what is seen in FIG. 4. In some embodiments, shaft 218 may be made from a polymer that is extruded or molded (e.g., injection or other types of molding) into the desired shape.

Figure 5:
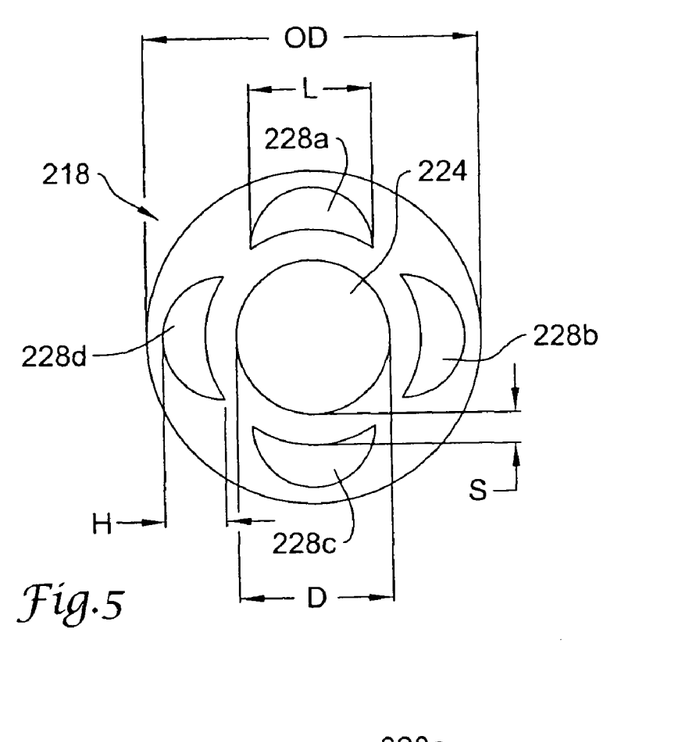
FIG. 5 is a cross-sectional view of the catheter shaft taken through line 5-5 of FIG. 4.
Figure 6:
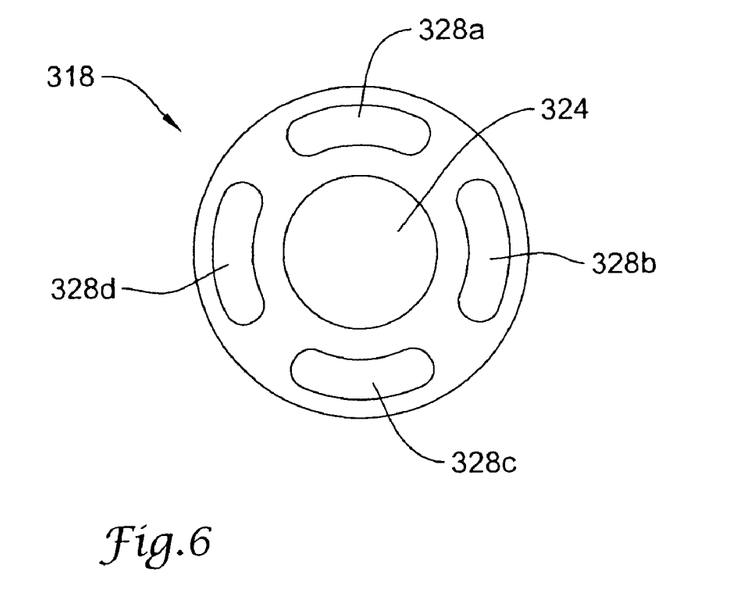
FIG. 6 is a cross-sectional view of another example catheter shaft.

A cross-sectional view of shaft 218 is shown in FIG. 5. Here, some of the suitable shapes and dimensions of the various structural elements of shaft 218 can be observed. For example, shaft 218 may be generally cylindrical in shape and have an outside diameter (OD) of about 0.04 to about 0.06 inches or so. The diameter (D) of lumen 24 may be about 0.022 to about 0.028 inches. In at least some embodiments, lumens 228*a/b/c/d* have a cross-sectional area that is generally half-moon shaped or semi-circular. The length (L) of lumens 228*a/b/c/d*, for example, may be on the order of about 0.005 to about 0.025 inches or more and the height (H) of lumens 228*a/b/c/d*, for example, may be on the order of about 0.004 to about 0.010 inches or more. Lumens 228*a/b/c/d* may be spaced a distance (S) of about 0.005 to about 0.010 inches or so from lumen 224. It can be appreciated that the above dimensions are intended to be illustrative in nature and should not be interpreted to limit Although FIG. 5 illustrates lumens 228*a/b/c/d* as being generally half-moon shaped, essentially any suitable shape may be used. For example, FIG. 6 illustrates a cross-sectional view of another example shaft 318, similar to shaft 218, where lumens 328*a/b/c/d* have a cross-sectional area that is more cylindrical in shape or is more pill-shaped. Generally, the shape of lumens 328*a/b/c/d* are similar to lumens 228*a/b/c/d*, but with rounded ends.

It should be understood that this disclosure is, in many respects, only illustrative. Changes may be made in details, particularly in matters of shape, size, and arrangement of steps without exceeding the scope of the invention. The invention's scope is, of course, defined in the language in which the appended claims are expressed.

What is claimed is:

1. A medical device, comprising:
    an elongate catheter shaft, the shaft including an inner tubular member having an inner lumen extending therethrough, an outer tubular member, and an inflation lumen disposed between the inner tubular member and the outer tubular member;
    wherein the outer tubular member includes a plurality of distal openings;
    a balloon coupled to the shaft and disposed over the distal openings in the outer tubular member; and
    one or more cutting members coupled to the balloon,
    wherein the plurality of distal openings are arranged about the outer tubular member in one or more longitudinally aligned sets, and
    wherein the one or more cutting members are radially aligned with the longitudinally aligned sets.

2. The medical device of claim 1, wherein the inner tubular member extends distally beyond a distal end of the outer tubular member.

3. The medical device of claim 1, wherein a distal end of the inner tubular member and a distal end of the outer tubular member are substantially aligned.

4. An angioplasty balloon catheter, comprising:
    a catheter shaft having an inflation lumen extending at least partially therethrough;
    a first set of longitudinally aligned openings defined in the shaft;
    a second set of longitudinally aligned openings defined in the shaft;
    a balloon coupled to the shaft and disposed over the sets of openings, the balloon including an inner chamber in fluid communication with the inflation lumen;
    a first cutting member coupled to the balloon and radially aligned with the first set of longitudinally aligned openings; and
    a second cutting member coupled to the balloon and radially aligned with the second set of longitudinally aligned openings.

5. The catheter of claim 4, wherein the shaft includes an inner tubular member and an outer tubular member, and wherein the inflation lumen is defined by a space between the inner and outer tubular members.

6. The catheter of claim 5, wherein the inner tubular member extends distally beyond a distal end of the outer tubular member.

7. The catheter of claim 5, wherein a distal end of the inner tubular member and a distal end of the outer tubular member are substantially aligned.

8. The catheter of claim 5, wherein the catheter shaft includes a central guidewire lumen, and wherein the inflation lumen is disposed in the catheter shaft and positioned radially from the guidewire lumen.

9. The catheter of claim 8, further comprising a second inflation lumen disposed in the catheter shaft and positioned radially from the guidewire lumen.

10. The catheter of claim 9, wherein the inflation lumen is in fluid communication with the first set of longitudinally aligned slots and wherein the second inflation lumen is in fluid communication with the second set of longitudinally aligned slots.

11. The catheter of claim 10, further comprising one or more inflation lumens disposed in the catheter shaft.

12. A cutting balloon catheter, comprising:
   an elongate shaft having a proximal end, a distal end, and a guidewire lumen extending therethrough;
   a first side lumen defined in the shaft and extending therethrough;
   a first longitudinally-aligned set of openings defined in the shaft and in fluid communication with the first side lumen;
   a second side lumen defined in the shaft and extending therethrough;
   a second longitudinally-aligned set of openings defined in the shaft and in fluid communication with the second side lumen;
   a balloon coupled to the shaft and disposed over the first and second sets of openings; and
   a cutting member coupled to the balloon.

13. The catheter of claim 12, wherein first set of openings includes three or more openings.

14. The catheter of claim 12, wherein the first side lumen has a half-moon shaped cross-sectional area.

15. The catheter of claim 12, wherein the first side lumen has a pill shaped cross-sectional area.

16. The catheter of claim 12, further comprising one or more additional side lumens.

17. The catheter of claim 12, wherein the first set of openings is radially aligned with the cutting member.

18. The catheter of claim 17, further comprising a second cutting member that is attached to the balloon and that is radially aligned with the second set of openings.

19. A cutting balloon catheter, comprising:
   a multi-lumen catheter shaft having a proximal end, a distal end, a central guidewire lumen extending therethrough, and a plurality of side lumens extending at least partially therethrough;
   a first set of openings defined in the shaft and in fluid communication with one of the plurality of side lumens;
   a second set of openings defined in the shaft and in fluid communication with another one of the plurality of side lumens;
   a balloon coupled to the shaft and disposed over the first and second sets of openings; and
   a cutting member coupled to the balloon.

20. The catheter of claim 19, wherein first set of openings includes three or more openings.

21. The catheter of claim 19, wherein the side lumens have a half-moon shaped cross-sectional area.

22. The catheter of claim 19, wherein the side lumens have a pill shaped cross-sectional area.

23. The catheter of claim 19, wherein the catheter shaft includes four side lumens.

24. The catheter of claim 19, wherein the first set of openings is radially aligned with the cutting member.

25. The catheter of claim 24, further comprising a second cutting member that is attached to the balloon and that is radially aligned with the second set of openings.

* * * * *